United States Patent [19]
Eppstein et al.

[11] Patent Number: 5,860,421
[45] Date of Patent: Jan. 19, 1999

[54] APPARATUS AND METHOD FOR CALIBRATING MEASUREMENT SYSTEMS

[75] Inventors: Jonathan A. Eppstein, Atlanta; Mark A. Samuels, Norcross; Keith D. Ignotz, Duluth, all of Ga.

[73] Assignee: SpectRx, Inc., Norcross, Ga.

[21] Appl. No.: 587,949

[22] Filed: Jan. 17, 1996

[51] Int. Cl.⁶ ................................................... A61B 8/00
[52] U.S. Cl. ...................................................... 128/660.06
[58] Field of Search ................ 128/660.06, 660.07; 178/18; 250/491.1; 73/620, 621; 367/140; 378/18, 207; 355/20, 81

[56] References Cited

U.S. PATENT DOCUMENTS

| | | | |
|---|---|---|---|
| 3,677,652 | 7/1972 | Little | 356/183 |
| 4,322,164 | 3/1982 | Shaw et al. | 356/243 |
| 4,360,270 | 11/1982 | Jeck | 356/243 |
| 4,495,413 | 1/1985 | Leroche et al. | 250/252.1 |
| 4,499,375 | 2/1985 | Jaszczak | 250/252.1 |
| 4,500,782 | 2/1985 | Allemann et al. | 250/291 |
| 4,642,422 | 2/1987 | Garwin et al. | 178/18 |
| 4,700,708 | 10/1987 | New et al. | 128/633 |
| 4,744,656 | 5/1988 | Moran et al. | 356/243 |
| 4,770,179 | 9/1988 | New et al. | 128/633 |
| 4,796,633 | 1/1989 | Zwirkoski | 128/634 |
| 4,847,493 | 7/1989 | Sodal et al. | 250/252.1 |
| 4,914,720 | 4/1990 | Knodle et al. | 250/343 |
| 4,975,581 | 12/1990 | Robinson et al. | 250/339 |
| 4,981,355 | 1/1991 | Higgins | 356/243 |
| 5,030,986 | 7/1991 | Dwyer et al. | 355/20 |
| 5,311,273 | 5/1994 | Tank et al. | 356/43 |
| 5,337,289 | 8/1994 | Fashing et al. | 367/140 |
| 5,365,925 | 11/1994 | Lee | 128/634 |
| 5,371,358 | 12/1994 | Chang et al. | 250/226 |
| 5,416,816 | 5/1995 | Wenstrup et al. | 378/18 |

FOREIGN PATENT DOCUMENTS 747 002 A1   11/1996   European Pat. Off. .......... A61B 5/00

*Primary Examiner*—George Manuel
*Attorney, Agent, or Firm*—Flesher & Kim

[57] ABSTRACT

A disposable calibration device is used to calibrate a measurement system which transmits radiation or acoustic waves to a material or tissue in order to effect measurements. The disposable calibration device includes a structure with a window through which the radiation or acoustic waves can be transmitted, as well as a removable calibration target arranged on the window and capable of returning a portion of the radiation or acoustic waves for calibrating the measurement system. The removable calibration target can be peeled from window to allow a measurement to be made on the material or tissue. Once a measurement is complete, the disposable calibration device can be discarded and a new calibration device can be inserted on the measuring system.

23 Claims, 11 Drawing Sheets

APPARATUS AND METHOD FOR CALIBRATING MEASUREMENT SYSTEMS

BACKGROUND OF THE INVENTION

1. Field of the Invention

This invention relates generally to an apparatus and method for calibrating measurement instruments of various types, and in particular to a disposable calibration device and method which uses that device for calibrating measurement instruments that perform measurements on a material or tissue. The calibration device includes a calibration target that ensures proper calibration of the measurement instrument, prevents scratching of windows through which measurements are taken, and also prevents reuse of the disposable calibration target, thereby helping to control the spread of infection if measurements are on tissues, and helping to prevent contamination if measurements are on materials.

2. Background of the Related Art

Many measurement systems require that calibrations be performed on a routine basis in order to compensate for changes in instrument performance and response. This is true for both radiation based measurement systems, i.e., systems that send electromagnetic radiation to the tissue or material to be measured and then detect the return radiation, and acoustic based measurement systems, i.e., systems that send acoustic waves or energy to the tissue or material to be measured and then detect the return acoustic signal. The calibration techniques in both cases typically involve measuring the response of a test target which has characteristics that remain stable with time and over a range of temperatures. Those techniques can also be used to compensate for instrument to instrument variations and any changes that an individual instrument may experience over its working lifetime. Often such measurement systems must be periodically calibrated and sometimes must be calibrated prior to each and every use. This calibration becomes especially important when measurements are made for medical or other critical applications.

Radiation measuring systems are currently used for a wide variety of purposes including to evaluate tissue or materials. These measuring systems require calibration for a variety of reasons including variations in the radiation source intensity, changes in spectral characteristics of the tissue or material, component aging and cleanliness, changes in temperature, radiation detector sensitivity changes, and electronic drifting.

Examples of radiation type measurement systems that often require some type of calibration include but are not limited to spectrometers, laser radar, radar or any other radiation measuring instrument that outputs radiation to a tissue or material and then measures some aspect of the return signal.

Acoustic type measuring systems are also used for a wide variety of purposes including to evaluate tissue or materials. Often these measurement systems must also be periodically calibrated and sometime must be calibrated prior to each use. Acoustic measurement systems also require calibration for a variety of reasons including variations in the output energy of the acoustic wave source, changes in spectral characteristics of the tissue or material, changes in temperature, detector sensitivity changes, and electronic drifting.

Examples of acoustic type measurement systems that often require some type of calibration include acoustic spectrometers, and interferometers or any other system which uses an acoustic wave measuring instrument that outputs acoustic energy to a material and then measures some portion of the return signal.

Various types of calibration techniques and devices have been attempted. For example, U.S. Pat. No. 5,365,925 describes a calibration boot which includes a plurality of materials, which is placed over an optical catheter for the purpose of making a multi-point calibration of reflected or backscattered light. U.S. Pat. No. 5,311,273 describes a method of using four black body radiators to provide calibration of an infrared spectrometer. However, neither of these approaches involves an inexpensive calibration target that can be easily discarded after each use, and thus does not prevent a user from taking a measurement without going through a calibration step.

U.S. Pat. No. 4,981,355 describes a calibration device for the in vitro calibration of a light guide, whereby a polyethylene material has a plurality of light scattering particles and a plurality of light absorbing particles which yields a neutral density filtering type of effect, uniformly distributing light in the plastic parts of the calibrator. The calibrator can be positioned into a sterile tray which is protected by a tear off plastic cover. Once the calibration is complete, the surgeon removes the catheter from the calibrator and the tray in which it is held and then presumably disposes of the calibration device and its tray. This approach, however, is neither simple nor inexpensive.

U.S. Pat. No. 4,796,633 describes a calibration reference apparatus that fits over a light guide. A stop limits the extent to which the light guide can be advanced into the cavity whereby an endface of the light guide is spaced from a region of the surface to define a gap. The end wall and the gap are adapted to return a known ratio of the light directed into the gap from the end face of the light guide. Again, however, this approach does not involve an inexpensive, disposable calibration device.

U.S. Pat. No. 4,744,656 discloses a calibration boot that snaps into place over an optical catheter allowing calibration of the catheter before use. Once the calibration is complete, the boot is removed and the optical catheter is ready for use. Each new catheter comes with a new boot. However, the boot is not present during the measurement and there is no provision to prevent reuse of the boot.

SUMMARY OF THE INVENTION

An object, therefore, of the invention is to provide a calibration device for calibrating measurement systems.

Another object of the invention is to provide a disposable calibration device.

Another object of the invention is to provide a calibration device which can be inexpensively mass produced.

Another object of the invention is to provide a disposable calibration device that helps prevent infection of tissue to be measured.

Another object of the invention is to provide a calibration device which provides an optically clear, scratch-free window between the instrument and the tissue or material to be measured.

Another object of the invention is to provide a calibration device that serves to compensate for the effects of variations from one measuring instrument to another.

Another object of the invention is to provide a calibration device that serves to compensate for changes in properties of an individual optical instrument over time.

Another object of the invention is to provide a calibration device that serves to compensate for changes in temperatures.

One advantage of the system is that it utilizes a calibration device with a removable calibration target.

Another advantage of the system is that once used, the calibration device cannot be re-used, thereby ensuring against infection from one person to another person.

Another advantage of the invention is that it can be used in radiation type measurement systems.

Another advantage of the invention is that it can be used in acoustic type measurement systems.

Another advantage of the invention is that it helps reduce the possibility of contamination from one material to another material.

One feature of the invention is that it can utilize a spectrometer as an optical instrument according to one embodiment of the invention.

Another feature of the invention is that it utilizes a disposable calibration target comprised of material that has a stable or predictable signature.

Another feature of the invention is that it utilizes a calibration target that can be removed.

Another feature of the invention is that it has a window through which radiation can be transmitted to tissue or material to be measured.

Another feature of the invention is that it utilizes a calibration target that can be peeled away from the window.

Another feature of the invention is that the calibration target can have a tear tab which allows the calibration target to be easily handled without disturbing the window or calibration target in contact with the window.

Another feature of the invention is that the calibration target is attached to the window by static cling brought about by a proper selection of materials for the window and the calibration target.

Another feature of the invention is that the calibration device can include a structure which can be cone-shaped.

Another feature of the invention is that the cone-shaped structure has a proximal end that attaches to the measuring instrument with which it is used.

Another feature of the invention is that the calibration device can include an outer annulus which comes into contact with the tissue or material to be measured.

Another feature of the invention is that the calibration device can include a landing annulus which aids in arranging the window on the tissue or material for taking a measurement.

These and other objects, advantages and features are accomplished by the provision of a calibration device for use with a measurement system which transmits radiation to a material or tissue in order to effect measurements, including: a structure including a window through which the radiation can be transmitted; and a removable calibration target arranged on the window and capable of returning a portion of the radiation for calibrating the measurement system, whereby the removable calibration target can be removed from the window to allow a measurement to be made on the material or tissue.

The removable calibration target can include a tear tab which can be gripped to remove the removable calibration target from the window.

The calibration device can act as a barrier between the material or tissue and the measurement system, which, if used as a medical instrument can help reduce the chance of infection.

The calibration device can include an outer annular ring attached thereto, whereby the outer annular ring comes into contact with the tissue or material.

The calibration device can further comprise a landing attachment attached to the structure, wherein the landing attachment comprises a landing annulus, which can be an extension of the window.

The calibration device can also comprise a ridge for maintaining the removable calibration target on the window.

The above and other objects, advantages and features are further accomplished by the provision of a method for calibrating a measurement system that outputs radiation from an output end, including: placing a calibrating device over the output end of the measuring system, wherein the calibration device has a removable calibration target; activating a calibration measurement; and removing the removable calibration target from the calibration device.

The above and other objects, advantages and features are also accomplished by the provision of a calibration device for use with a measurement system which transmits acoustic waves to a material or tissue in order to effect measurements, comprising: a structure including a window through which the acoustic waves can be transmitted; and a removable calibration target arranged on the window and capable of reflecting and/or scattering a portion of the acoustic waves for calibrating the measurement system, whereby the removable calibration target can be removed from the window to allow a measurement to be made on the material or tissue.

The above and other objects, advantages and features are also accomplished by the provision of a calibration device for use with a measurement system which transmits radiation to a material or tissue in order to effect measurements, comprising: a structure through which the radiation can be transmitted; and a removable calibration target arranged on the structure so as to partially return a portion of the radiation for calibration, whereby the removable calibration target can be removed from the structure to allow a measurement to be made on the material or tissue.

The above and other objects, advantages and features are also accomplished by the provision of a method for performing a calibrated measurement on tissue or material using a measurement system that outputs radiation from an output end, comprising: placing a calibrating device over the output end of the measuring system, wherein the calibration device has a removable calibration target; activating a calibration measurement; removing the removable calibration target from the calibration device; and performing a measurement on the tissue or material using the calibration measurement to provide the calibrated measurement on the tissue or material.

These and other objects, advantages and features will become more apparent from the following description of embodiments thereof taken in conjunction with the accompanying drawings.

BRIEF DESCRIPTION OF THE DRAWINGS

FIGS. 5B and 5C show the calibration target removed.

DETAILED DESCRIPTION OF PREFERRED EMBODIMENTS

Figure 1A:
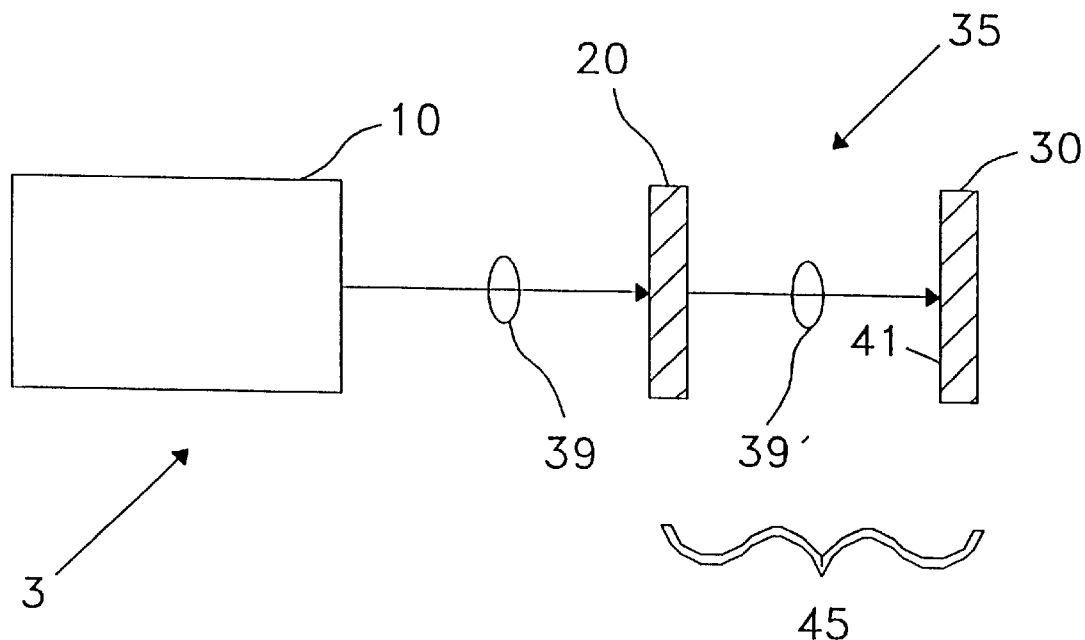
FIG. 1A shows a schematic view of a measurement system in a calibration mode.

FIG. 1A is a schematic view of a system 3 in a calibration mode. System 3 includes an instrument 10 which transmits electro-magnetic radiation 39. Alternatively, instrument 10 can be an instrument which transmits acoustic waves. Reference number 39 will be used to represent electromagnetic radiation or acoustic radiation just as reference number 10 will be used to represent an instrument that outputs either electromagnetic radiation 39 or acoustic waves 39. If instrument 10 outputs electromagnetic radiation 39, that radiation can lie within the visible, infrared, ultra-violet regimes, and/or within the rf, microwave and millimeter wave regimes. With regard to electromagnetic radiation 39, instrument 10 can be a spectrometer, laser radar, radar or any other radiation measuring instrument that outputs radiation to a material 40 and then measures some portion of the return signal. With regard to acousto-optic waves 39, instrument 10 can be an acoustic measuring/imaging device that outputs acoustic waves and measures the return acoustic wave signal. The discussion that follows is drawn to electromagnetic radiation 39, it being understood that an analogous discussion applies for the case in which acoustic waves are output from instrument 10. Radiation 39 is transmitted toward and through shield 20 toward a calibration target 30. Shield 20 serves as a barrier between instrument 10 and material or tissue 40 to be measured and hence functions to reduce contamination of material or tissue 40. One major (but not the only) purpose of shield 20 is to guard against possible infection when living tissue 40 is measured. Hence, shield 20 might also be referred to as an infection shield.

Shield 20 must be at least partially transmissive to radiation 39 such that a portion thereof.appears as radiation 39'. Radiation 39' passes through region 35 and reaches surface 41 of calibration target 30. Surface 41 can be the same material as calibration target 30 or a specially applied layer. Also, region 35 can be a variety of adhesives, gels, pastes, or other materials. The combination of shield 20, region 35 and calibration target 30 comprise calibration device 45. Once system 3 with instrument 10 is calibrated, calibration target 30 is removed, and system 3 is now ready to take measurements on material 40 through shield 20.

Figure 1B:
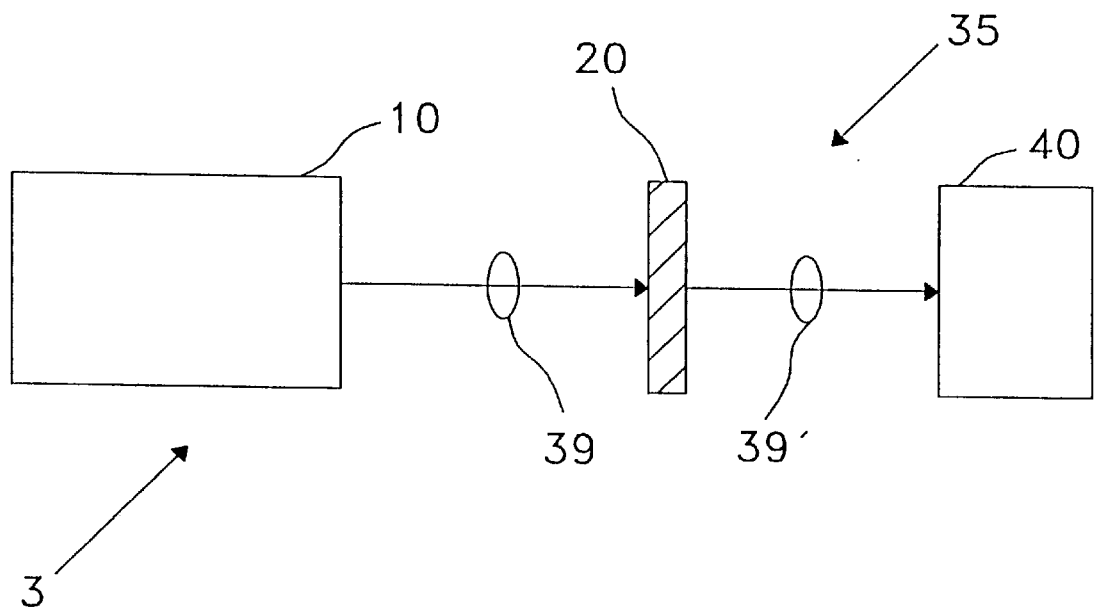
FIG. 1B shows the same system in a measurement mode wherein the calibration target has been removed and radiation is now reaching the tissue or material to be measured.

FIG. 1B shows system 3 in measurement mode in that calibration target 30 has been removed and radiation 39' is now reaching tissue or material 40 to be measured through shield 20.

With regard to electromagnetic radiation 39, instrument 10 can be a spectrometer, laser radar, radar or any other radiation measuring instrument that outputs radiation to a material 40 and then measures some portion of the return signal. With regard to acousto-optic waves 39, instrument 10 can be a acoustic measuring/imaging device that outputs acoustic waves and measures the return acoustic wave signal.

Figure 2A:
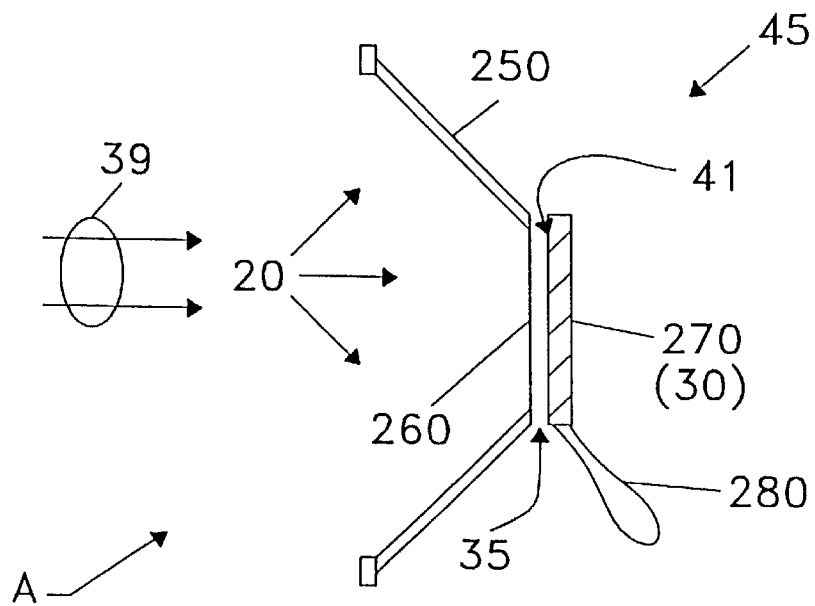
FIG. 2A shows a schematic representation of a preferred embodiment of the calibration device used in the calibration mode.

FIG. 2A shows a schematic representation of a preferred embodiment of device 45 used in the calibration mode for an instrument 10 (not shown). Device 45 includes shield supporting structure 250 with window 260 (structure 250 and window 260 comprising shield 20 from FIG. 1A). In this embodiment, supporting structure 250 has a cone-type shape cut off at top 265 and window 260 is circular shaped and is arranged to cover top 265. It should be understood, however, that the shape of structure 250 need not be limited to this cone-type shape and window 260 need not be limited to a circular shape. Finally, device 45 includes calibration target 270 (corresponding to target 30 from FIG. 1A) with tab 280.

Device 45 receives radiation 39 (which will be considered from here on out to be essentially the same as radiation 39' in accordance with a preferred embodiment) from instrument 10 which passes through window 260 and region 35 and then reaches surface 41 of calibration target 270. Window 260 must be at least partially and preferably nearly completely transparent to radiation 39. Region 35 can be an adhesive, gel, liquid and/or free space. A preferred embodiment, however, has window 260 statically charged with respect to surface 41 of calibration target 270, thereby holding calibration target 270 in place. Radiation 39 is then incident on surface 41 of calibration target 270.

Calibration target 270 should be selected to have a known reflection spectrum for calibration purposes. For instruments 10 which perform measurements of intensity independent of wavelength, a high reflection surface 41 of calibration target 270 may be advantageous. This might include radar, laser radar and interferometric type instruments. Note however, that such instruments might also benefit from other lower reflecting calibrating surfaces 41 of calibration target 270 as well. Instruments 10 such as spectrometers should use calibration targets that have a well defined or known spectral characteristic.

Figure 2B:
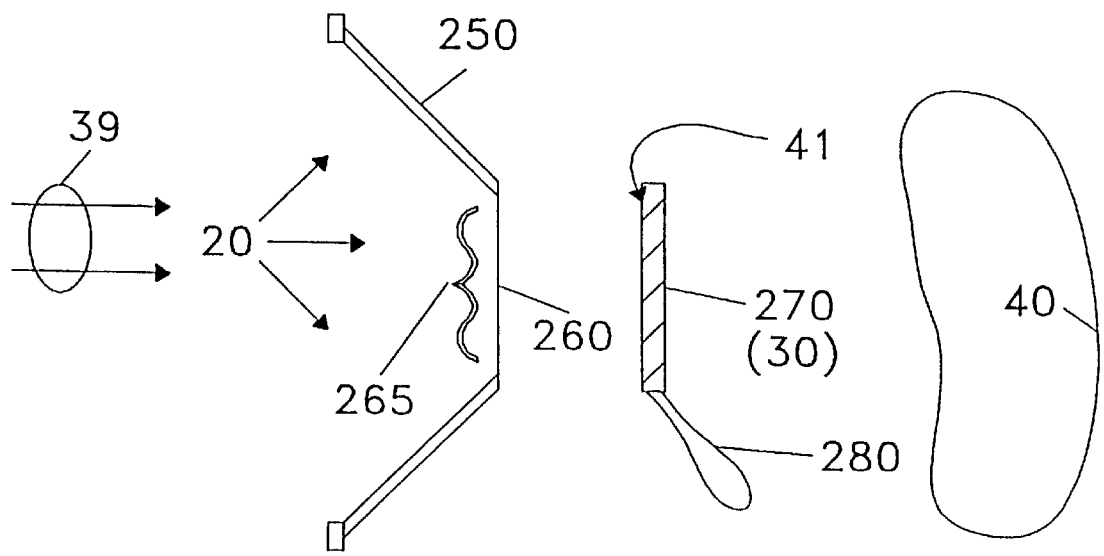
FIG. 2B shows the calibration device after the calibration target is removed (peeled) from the window.

Once system 3 with instrument 10 is calibrated, calibration target 270 is removed (peeled) from window 260 by pulling on a tear tab 280 as shown in FIG. 2B. Tear tab 280 allows the user to remove the calibration target 270 from shield window 260 of shield 20. System 3 is now ready to take measurements on material 40 through window 260.

Figure 3A:
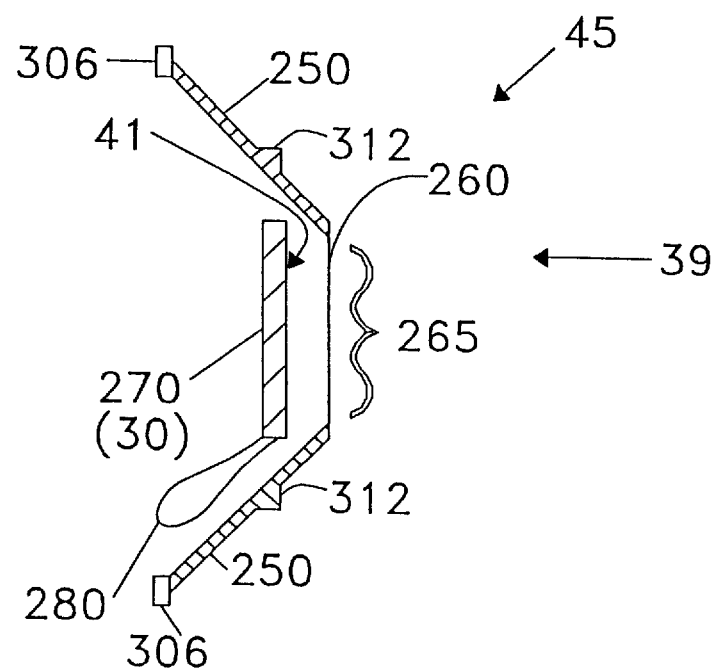
FIGS. 3A and 3B correspond to FIGS. 2A and 2B, but with the radiation entering from the right hand side and the calibration target is attached to the window within the structure.
Figure 3B:
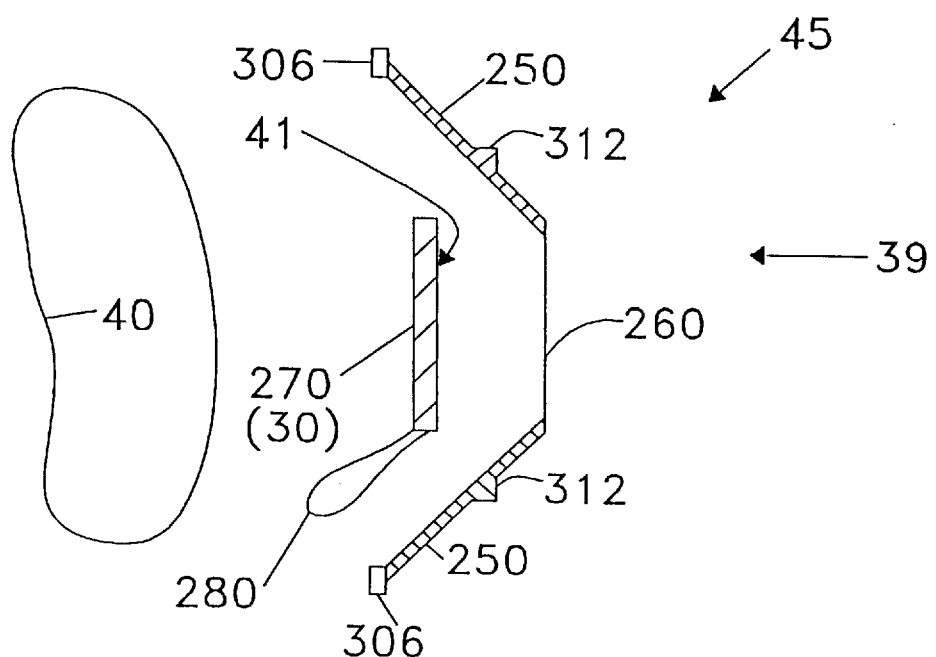

FIGS. 3A and 3B correspond to FIGS. 2A and 2B, but with radiation 39 entering from the right hand side and calibration target 270 attached to window 260 within structure 250. In this case, an outer annular ring 306 comes into contact with tissue or material 40 to be measured. Structure 250 includes an annular ring or ridge 312 which secures device 45 to instrument 10 (not shown).

Referring to FIGS. 3A and 3B, device 45 receives radiation 39 from instrument 10 which passes through window 260 and reaches surface 41 of calibration target 270. Again region 35 can be an adhesive, gel, liquid and/or free space, but a preferred embodiment, has window 260 statically charged with respect to surface 41 of calibration target 270, thereby holding calibration target 270 in place. Radiation 39 passes though window 260 to yield radiation 39' which is preferably identical to radiation 39. Radiation 39' then is incident on surface 41 of calibration target 270.

Once calibration has been completed, calibration target 270 is removed from window 260 using tear tab 280 as shown in FIG. 3B. Outer annular ring 306 is then arranged to contact tissue or material 40 for a measurement.

Figure 3C:
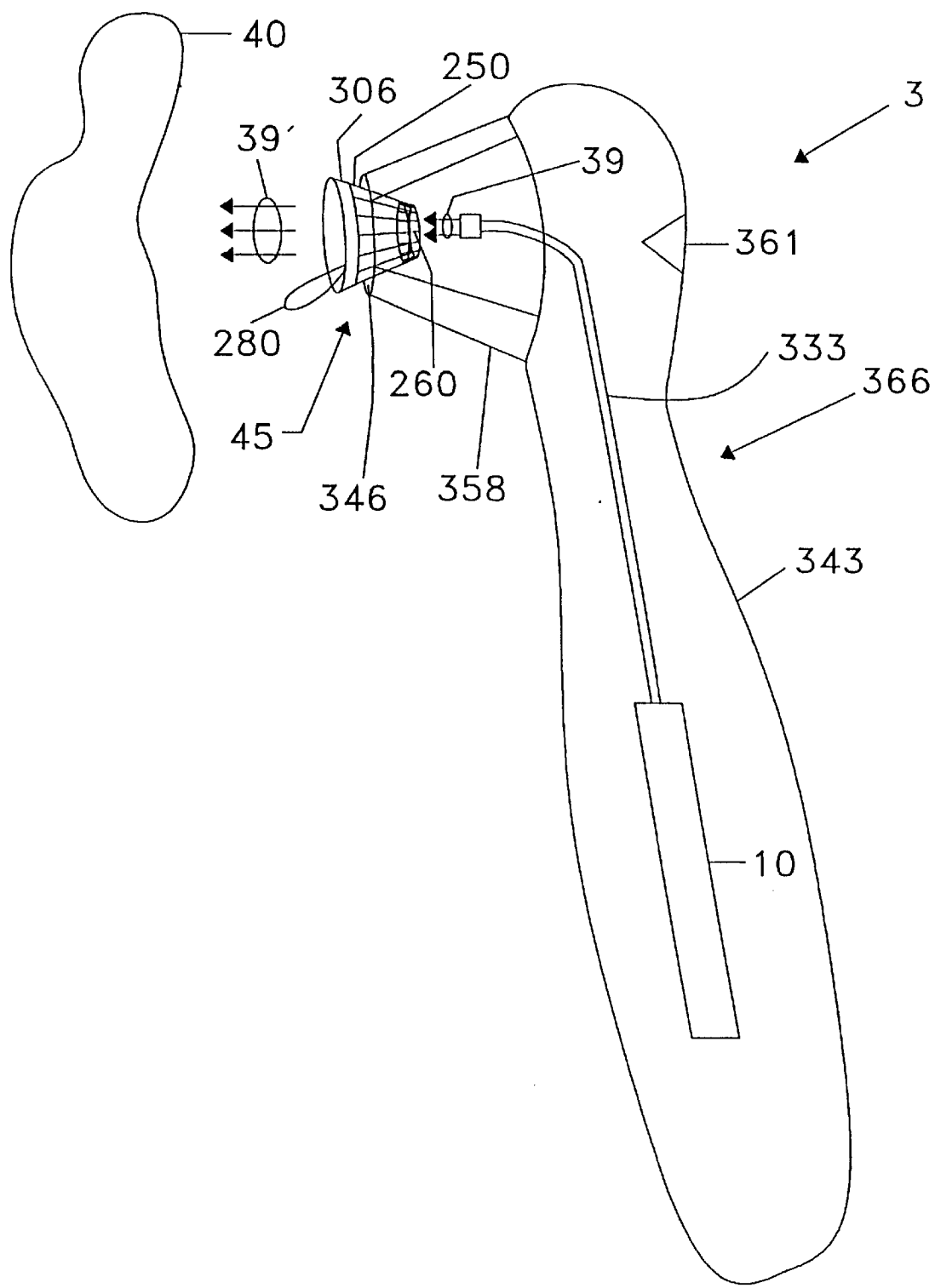
FIG. 3C shows a measurement system which utilizes a disposable calibration device as in FIGS. 3A and 3B.

FIG. 3C shows a measurement system 3 which utilizes a disposable calibration device 45 for instrument 10. Here, instrument 10 is an optical instrument such as a spectrometer and radiation 39 is optical radiation which can be in the visible, uv and/or infrared regions. System 3 includes a housing 343 which is approximately the size of a human hand. Instrument 10 is coupled to calibration device 45 via optical fiber 333. Calibration device 45 is inserted into an opening end 346 of cone-shaped holder 358 of housing 343. Curved portion 366 of housing 343 allows the hand to comfortably hold system 3. A person can initiate a calibration or measurement as the case may be, by pressing a push button 361 with his or her thumb. Once a calibration measurement has been performed, tear tab 280 maybe used to peel calibration target 270 away from window 260 (not shown in this view), and system 3 is now ready to make a measurement on material or tissue 40.

Figure 3D:
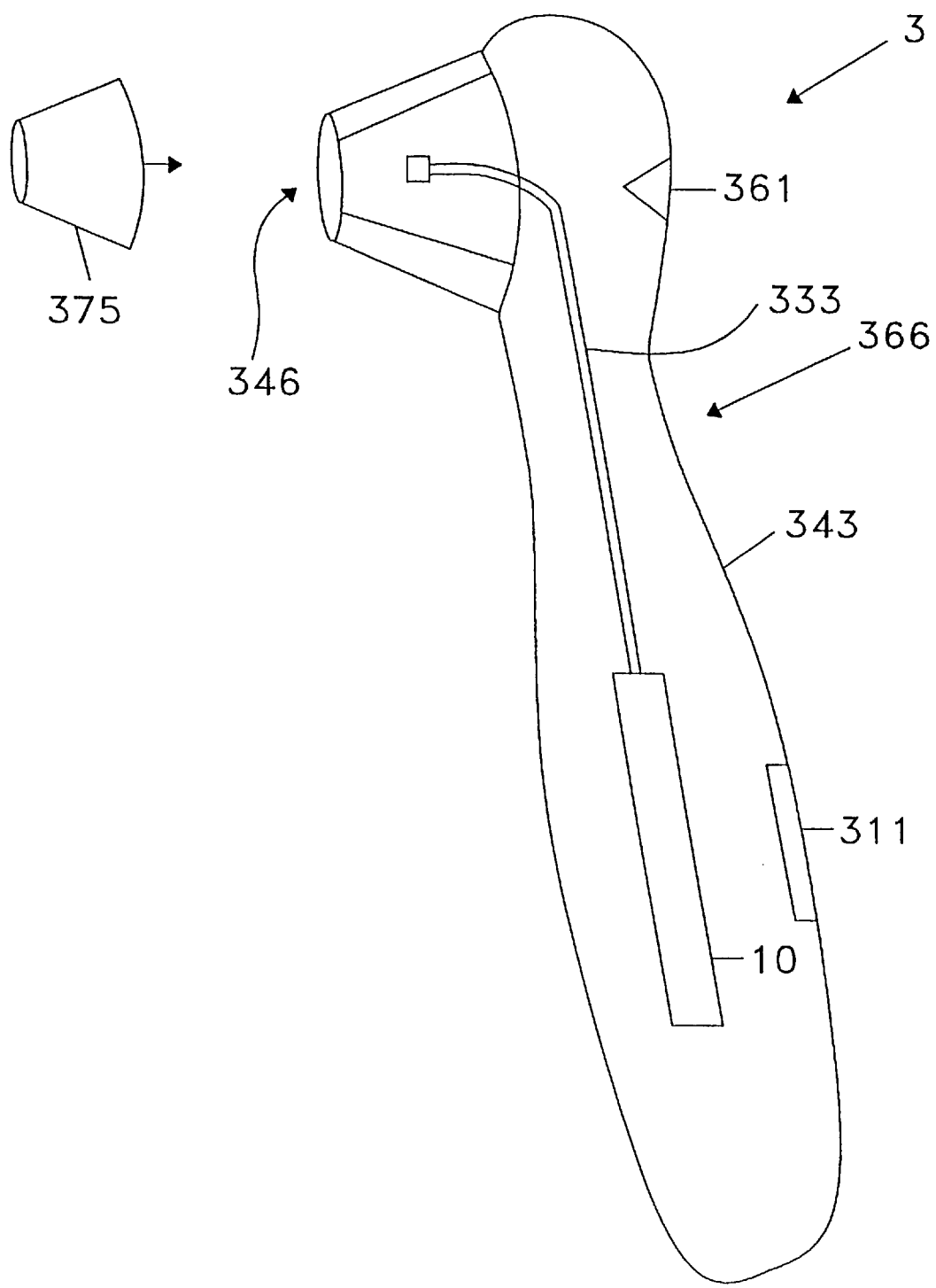
FIG. 3D shows the same measurement system with the calibration device removed.

FIG. 3D shows the same measurement system with calibration device 45 removed. A new calibration device 45 must be inserted into end 346 of system 3 and the above discussed process of calibration must be repeated and calibration target 270 peeled away before system 3 is ready to perform a new measurement. Alternatively, a cap 375 can be placed over end 346 between measurements.

In all of the above embodiments, calibration target 270 can have calibration information fitted directly on surface 41 of calibration target 270, and which can be read by instrument 10. This calibration information can include a message read by instrument 10 which initiates a system shut down after one or a predetermined number of measurements are performed. For the case of shut down upon a single measurement, contamination is avoided, because that system 3 cannot be reused on a new or different material or tissue until a new calibration device 45 replaces the used calibration device. In an alternative approach, this calibration information can be directly input into system 3 by a user using input 311.

Figure 3E:
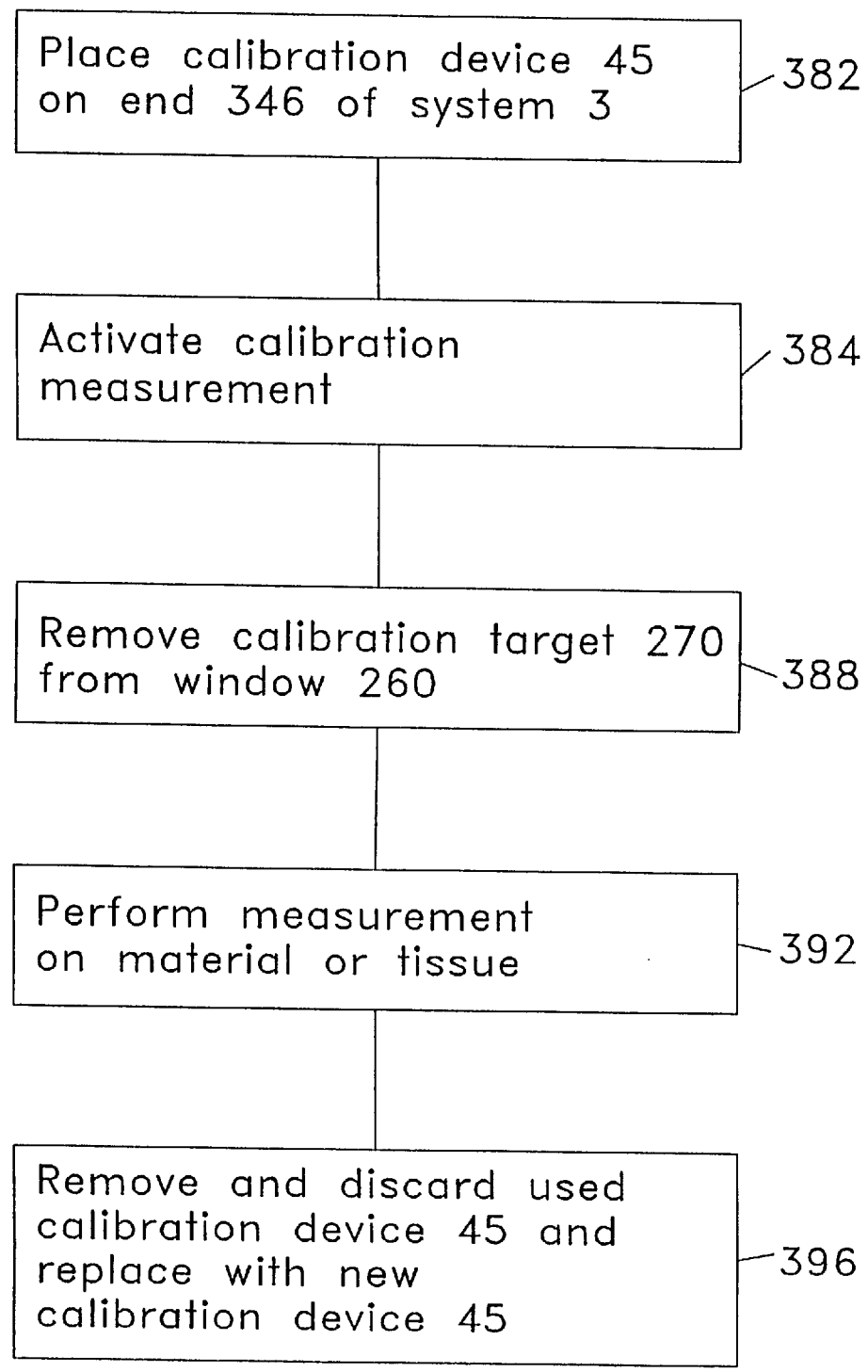
FIG. 3E summarizes the steps involved for calibrating the above measurement system and then taking a measurement on material or tissue.

FIG. 3E summarizes the steps involved for system 3 to take a measurement on material or tissue 40. In particular, step 382 involves placing calibration device 45 on end 346 of system 3. At this point, calibration device 45 still has calibration target 270 covering window 260. A calibration measurement is performed by system 3 at step 384 by pressing push button 361 which activates instrument 10. Step 388 involves removing calibration target 270 from window 260 using tear tab 280. Step 392 then involves performing a measurement on tissue or material 40 to be measured. This might involve a single measurement or multiple measurements (if cross contamination is not an issue) on the same or a similar tissue or material. That is, if measurements are being performed on a patient's tissue, several measurements might be repeated in the same vicinity of that patient's tissue. Similarly, if measurements are being made on some type of material, multiple measurements can be made in the vicinity of that measurement provided that cross contamination is not an issue. Finally, once the measurement or measurements have been completed, calibration device 45 is removed, discarded, and replaced with a new calibration device 45 at step 396. Alternatively, used calibration device 45 can be removed, discarded, and cap 375 can be placed over end 346 until a new measurement is to be made.

Figure 4A:
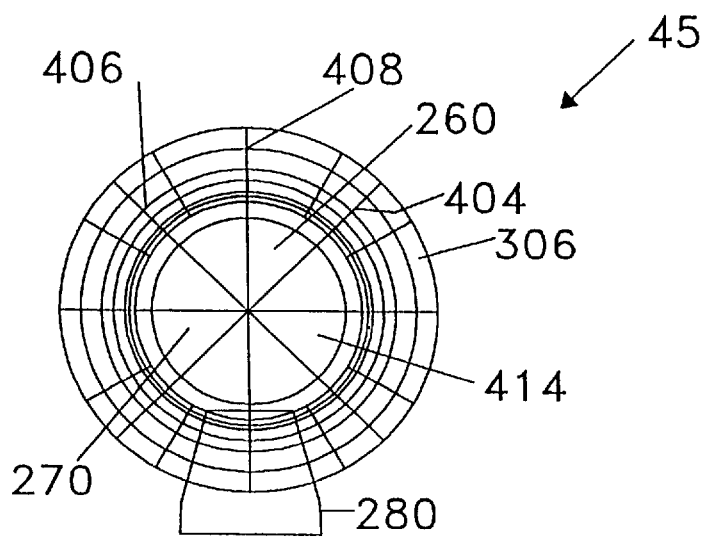
FIGS. 4A and 4B show a top view and a side view, respectively, of a calibration device similar to the calibration device in FIG. 3A.
Figure 4B:
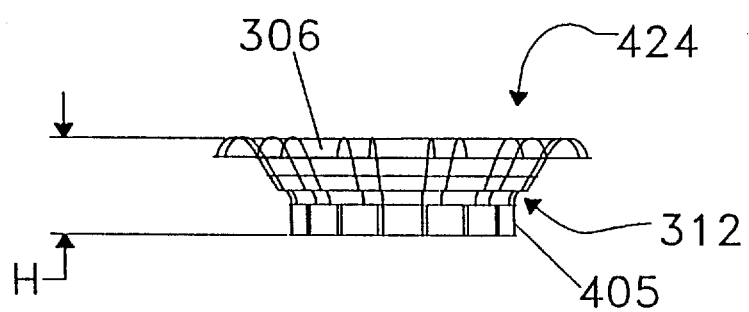
Figure 4C:
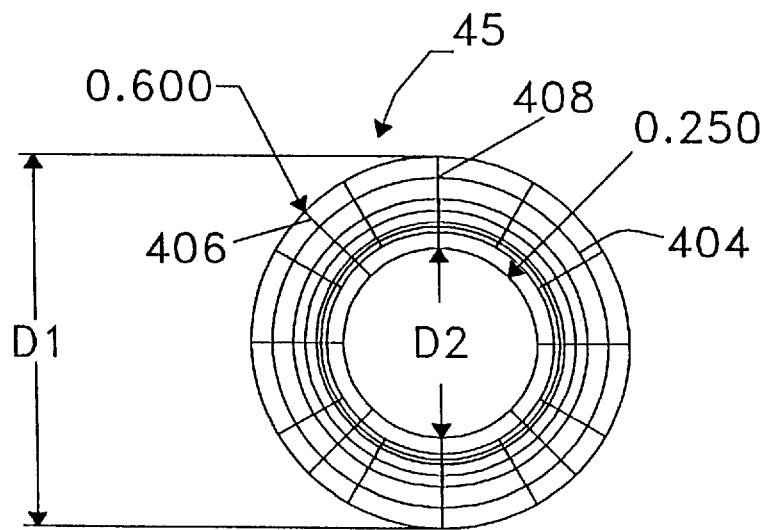
FIGS. 4C and 4D show the same views as FIGS. 4A and 4B, respectively, with the calibration target removed.
Figure 4D:
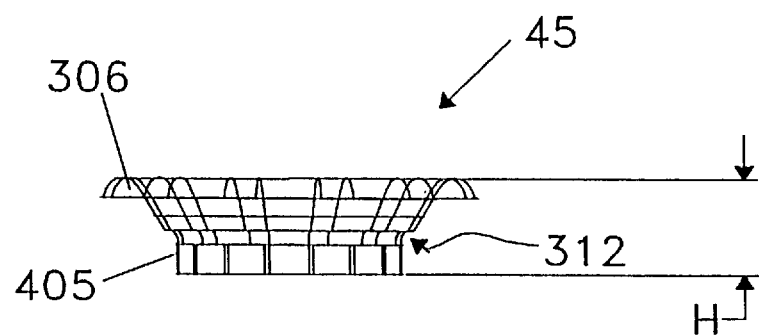

FIGS. 4A and 4B show a top view and a side view, respectively, of calibration device 45 similar, but not identical to device 45 of FIG. 3A. FIGS. 4C and 4D show the same views as FIGS. 4A and 4B, respectively, with calibration target 270 removed. Device 45 can include cross-hatched lines 404, 406, and 408. Lines 404, 406, and 408 can be placed on the backside 414 of calibration target 270 as well as along inner-sides 424 of structure 250 and outer annular ring 306 of calibration target 270 which can aid in the placement of window 260 on material or tissue 40. Device 45 in FIGS. 4B and 4D has annular ring 301 which contacts the material or tissue 40 to be measured.

Device 45 also has a collar section 405 that attaches to the optical outlet (not shown) of instrument 10. Diameter D1 is defined to be the diameter of annular ring 306 and diameter D2 is defined to be the diameter of window 260, and height H is defined to be the distance from window 260 to annular ring 306.

Figure 5A:
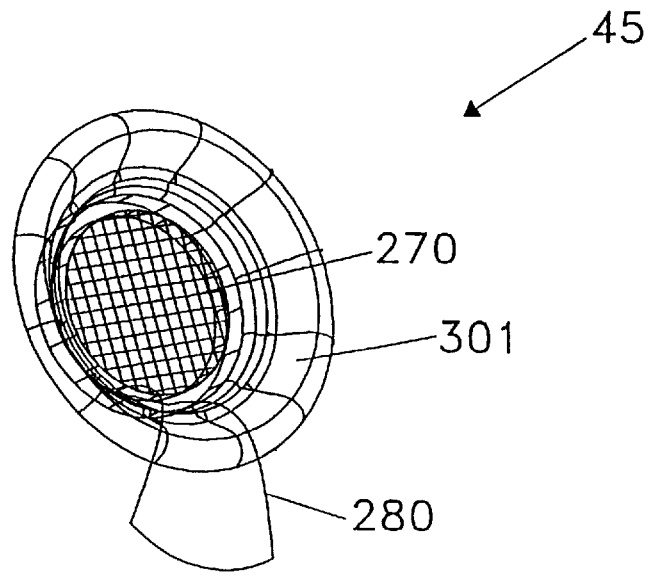
FIGS. 5A, 5B, and 5C show three more perspective views of the calibration device, where
Figure 5B:
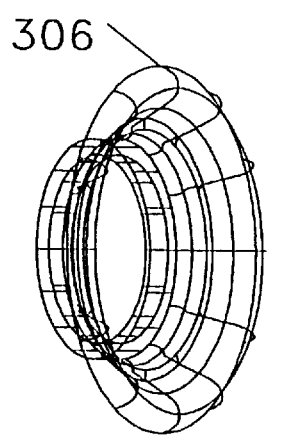
Figure 5C:
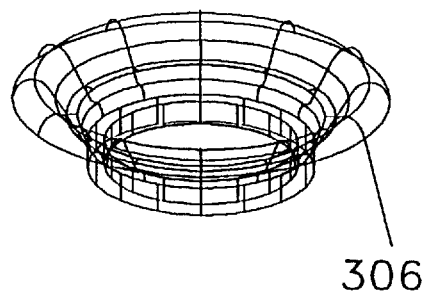

FIGS. 5A, 5B, and 5C show three more perspective views of device 45 (FIGS. 5B and 5C have calibration target 270 removed).

Figure 6:
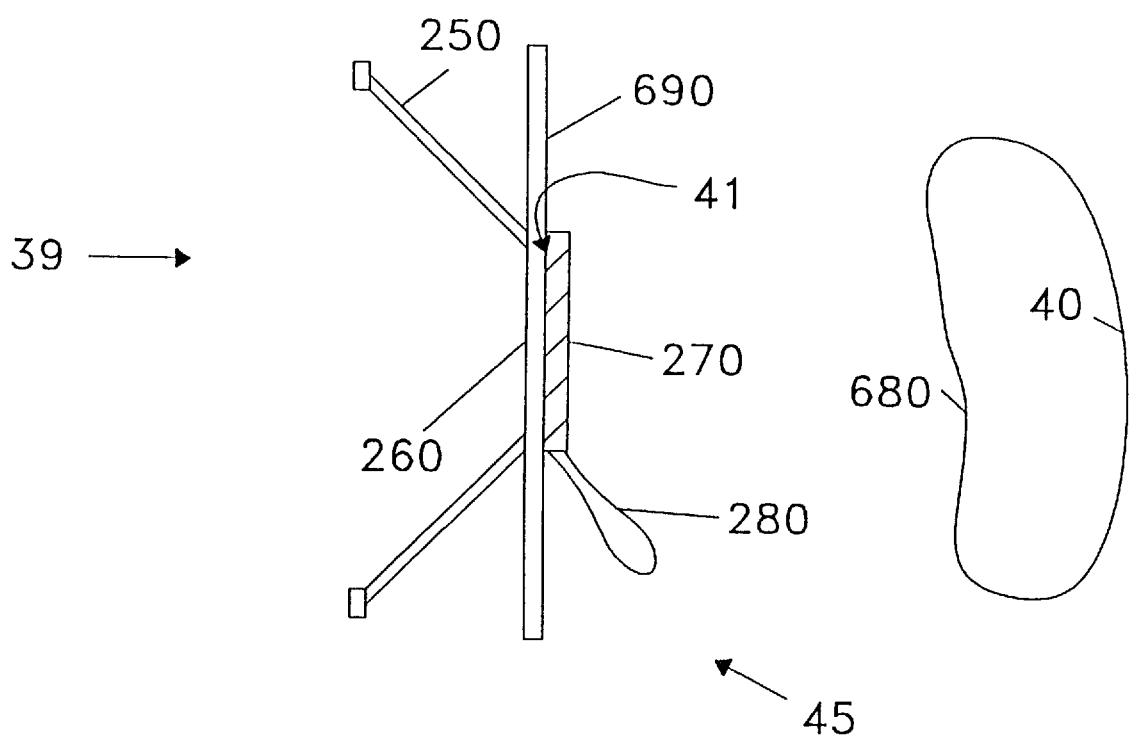
FIG. 6 shows a calibration device according to another embodiment of the invention.

FIG. 6 shows a calibration device 45 according to another embodiment of the invention. Here, a landing annulus 690 is affixed to structure 250. Landing annulus 690 serves to fix the angle at which radiation is incident on surface 680. Landing annulus 690 is preferably transparent to radiation 39. Calibration occurs as before with the presence of calibration target 270. A calibration is made and then calibration target 270 is removed and annulus 690 remains in place. Device 45 is then placed on surface 680 such that annulus 690 lies flat on surface 680, thereby ensuring that radiation 39 is incident approximately normal to surface 680 as it was to surface 41 of calibration target 270. On the other hand, depending on the type of measurement, it may be preferable due to unwanted spectral reflections, to have radiation 39 incident at an angle off normal to surface 680. Landing annulus 690 can be a separate piece affixed to structure 250 and comprised of any type of rigid material such as various plastics. If infection to surface 680 of tissue 40 is an issue, then landing annulus 690 should be removable from structure 250. Alternatively, annulus 690 can simply be an extension of window 260 itself.

Structure 250 is preferably fabricated from molded plastic with a smooth window zone defined for window 260. Using plastic molding allows structure 250 to be fabricated at low cost and in a wide variety of shapes and sizes. Calibration target 270 can also be fabricated from plastic and may also have a dye or other material added as surface 41 to provide sufficient spectral detail to effect the necessary calibration. Calibration target 270 can be attached to window section 260 in such a way that once removed, it cannot be readily re-attached. One implementation is to fabricate calibration target 270 using a statically clinging type plastic, and to fabricate structure 250 using an appropriate material such as an acrylic called polymethyl methacrylate (PMMA) both of which are available from 3M Corporation.

Figure 7A:
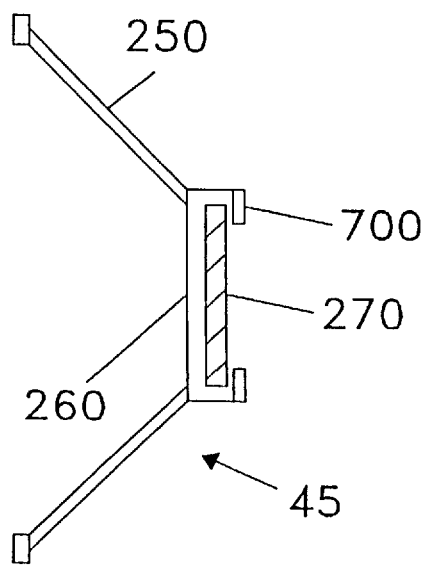
FIG. 7A shows a side view of the calibration device according to yet another embodiment of the invention.
Figure 7B:
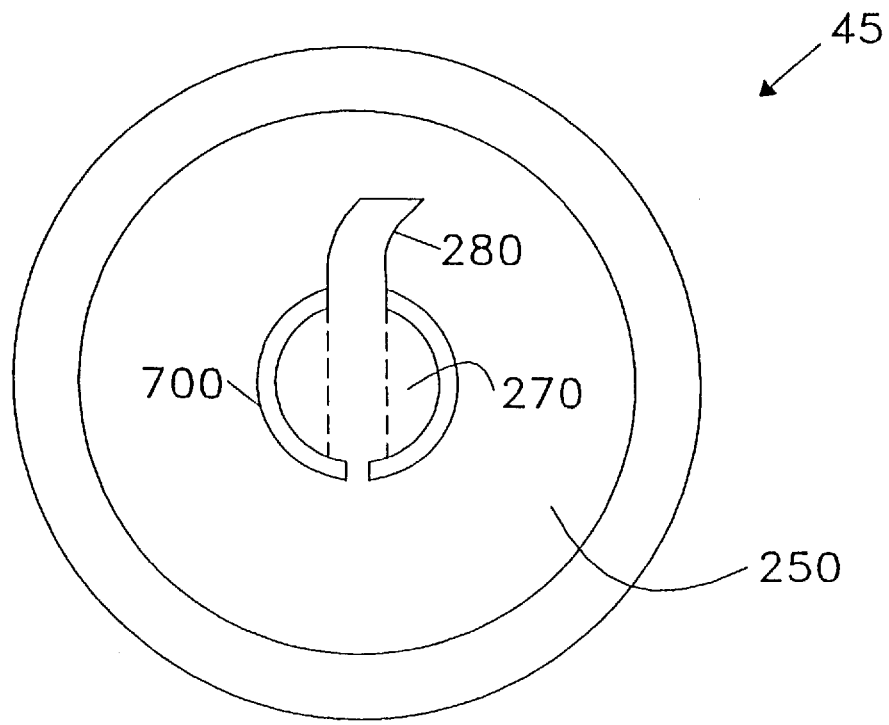
FIG. 7B shows the calibration device as viewed from above.

FIG. 7A shows a side view of calibration device 45 according to yet another embodiment of the invention. Here, calibration target 270 is held in place by ridge 700 alone or together with static cling between target 270 and window 260. Ridge 700 can be part of window 260 or a separate piece. FIG. 7B shows calibration device 45 as viewed from above.

Numerous and additional modifications and variations of the present invention are possible in light of the above teachings. It is therefore to be understood that within the scope of the appended claims, the invention may be practiced otherwise than specifically claimed.

What is claimed is:

1. A calibration device for use with a measurement system which transmits radiation to a material or tissue in order to effect measurements, comprising:

a structure through which the radiation can be transmitted; and a removable calibration target arranged on said structure, said removable calibration target capable of returning a portion of the radiation, the portion of the radiation returned for calibrating the measurement system, wherein said removable calibration target is to be removed from said structure to allow a measurement to be made on the material or tissue, and wherein said structure is interposed between the measurement system and the material or tissue when a measurement is made on the material or tissue.

2. The calibration device as claimed in claim 1, wherein said structure comprises a window of a material through which the radiation can pass.

3. The calibration device as claimed in claim 2 wherein said structure and said window comprise a barrier between the material or tissue and the measurement system.

4. The calibration device as claimed in claim 2 wherein said landing attachment comprises an extension of said window.

5. The calibration device as claimed in claim 2 wherein said window comprises a ridge for maintaining said removable calibration target on said window.

6. The calibration device as claimed in claim 1, wherein said removable calibration target includes a tear tab which can be gripped to remove said removable calibration target from said window.

7. The calibration device as claimed in claim 1, wherein said structure comprises an infection shield between the material or tissue and the measurement system.

8. The calibration device as claimed in claim 1, wherein said structure further comprises an outer annular ring attached thereto, wherein said outer annular ring comes into contact with the material or tissue in order to effect measurement on the material or tissue.

9. The calibration device as claimed in claim 1, further comprising a landing attachment attached to said structure.

10. The calibration device as claimed in claim 9, wherein said landing attachment comprises a landing annulus.

11. A method for calibrating a measurement system that outputs radiation from an output end of the measurement system, comprising the steps of:

placing a calibration device over the output end of the measurement system, wherein the calibration device includes a structure and a removable calibration target attached to the structure;

activating a calibration measurement;

removing the removable calibration target from the calibration device; and leaving the structure attached to the measurement system after the removable calibration target has been removed so that the structure will be interposed between the measurement system and a material or tissue upon which measurements will be performed.

12. A calibration device for use with a measurement system which transmits acoustic waves to a material or tissue in order to effect measurements, comprising:

a structure including a window through which the acoustic waves can be transmitted; and a removable calibration target arranged on said window and capable of reflecting and/or scattering a portion of said acoustic waves for calibrating the measurement system, whereby the removable calibration target can be removed from said window to allow a measurement to be made on the material or tissue.

13. The calibration device as claimed in claim 12, wherein said removable calibration target includes a tear tab which can be gripped to remove said removable calibration target from said window.

14. The calibration device as claimed in claim 12, wherein said structure and said window comprise a barrier between the material or tissue and the measurement system.

15. The calibration device as claimed in claim 12, wherein said structure and said window comprise an infection shield between the tissue and the measurement system.

16. The calibration device as claimed in claim 12, wherein said structure further comprises an outer annular ring attached thereto, whereby said outer annular ring comes into contact with the material or tissue in order to effect measurement on the material or tissue.

17. The calibration device as claimed in claim 12, further comprising a landing attachment attached to said structure.

18. The calibration device as claimed in claim 17, wherein said landing attachment comprises a landing annulus.

19. The calibration device as claimed in claim 17, wherein said landing attachment comprises an extension of said window.

20. The calibration device as claimed in claim 12, wherein said window comprises a ridge for maintaining said removable calibration target on said window.

21. A calibration device for use with a measurement system which transmits radiation to a material or tissue in order to effect measurements, comprising:

a structure through which the radiation can be transmitted; and a removable calibration target arranged on said structure so as to partially return a portion of the radiation for calibration of said measurement system, wherein said removable calibration target is removable from said structure to allow a measurement to be made on the material or tissue, and wherein the structure remains attached to measurement system and is to be interposed between the measurement system and the material or tissue when measurements are made on the material or tissue.

22. A method for performing a calibrated measurement on tissue or material using a measurement system that outputs radiation from an output end, comprising the steps of:

placing a calibration device over the output end of the measurement system, wherein the calibration device includes a calibration target removably attached to a structure;

activating calibration of the measurement system;

removing the calibration target from the calibration device; and performing a calibrated measurement on the tissue or material using the previous calibration measurement to determine the calibrated measurement of the tissue or material, wherein the structure acts as a barrier between the material or tissue and the measurement system.

23. A calibration device for use with a measurement system which transmits one of radiation and acoustic waves to a material or tissue to effect measurements on the material or tissue, comprising:

a structure through which the radiation or acoustic waves may pass; and a removable calibration target arranged on the structure, the removable calibration target being capable of returning a portion of the radiation or acoustic waves to the measurement system, wherein the removable calibration target includes a user graspable tab than can be used to remove the calibration target from the structure.

* * * * *